US00PP22543P2

(12) United States Plant Patent
Kearley

(10) Patent No.: US PP22,543 P2
(45) Date of Patent: Mar. 6, 2012

(54) *MANDEVILLA* PLANT NAMED 'FG1PK'

(50) Latin Name: *Mandevilla splendens*
Varietal Denomination: FG1PK

(75) Inventor: Dick Kearley, Hawthorne, FL (US)

(73) Assignee: Fury Genetics LLC, Hawthorne, FL (US)

( * ) Notice: Subject to any disclaimer, the term of this patent is extended or adjusted under 35 U.S.C. 154(b) by 0 days.

(21) Appl. No.: 12/931,678

(22) Filed: Feb. 7, 2011

(51) Int. Cl.
*A01H 5/00* (2006.01)

(52) U.S. Cl. ..... Plt./232

(58) Field of Classification Search ..... Plt./232
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'FG1PK', characterized by its upright, moderately vining and relatively compact plant habit; freely branching habit, dense and bushy appearance; marbled red purple and light red purple-colored flowers; and year-round flowering.

1 Drawing Sheet

Botanical designation: *Mandevilla splendens.*
Cultivar denomination: 'FG1PK'.

BACKGROUND OF THE INVENTION

The present invention relates to a new and distinct cultivar of *Mandevilla* plant, botanically known as *Mandevilla splendens* and hereinafter referred to by the name 'FG1PK'.

The new *Mandevilla* plant is a naturally-occurring branch mutation of *Mandevilla splendens* 'DIP 79', disclosed in U.S. Plant Pat. No. 19,698. The new *Mandevilla* plant was discovered and selected by the Inventor on a single plant within a population of plants of 'DIP 79' grown in a controlled greenhouse environment in Hawthorne, Fla. on Jan. 10, 2009. The new *Mandevilla* was selected on the basis of its unique flower coloration.

Asexual reproduction of the new *Mandevilla* plant by tip cuttings in a controlled greenhouse in Hawthorne, Fla. since Jan. 15, 2009, has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'FG1PK'. These characteristics in combination distinguish 'FG1PK' as a new and distinct *Mandevilla* plant:

1. Upright, moderately vining and relatively compact plant habit.
2. Freely branching habit, dense and bushy appearance.
3. Marbled red purple and light red purple-colored flowers.
4. Year-round flowering.

Plants of the new *Mandevilla* differ primarily from plants of the parent, 'DIP 79', in flower color as plants of 'DIP 79' have vibrant red-colored flowers.

Plants of the new *Mandevilla* can be compared to plants of the *Mandevilla* 'Red Riding Hood', not patented. In side-by-side comparisons plants of the new *Mandevilla* differ from plants of 'Red Riding Hood' in the following characteristics:

1. Plants of the new *Mandevilla* are less vining than plants of 'Red Riding Hood'.
2. Plants of the new *Mandevilla* have shorter internodes than plants of 'Red Riding Hood'.
3. Plants of the new *Mandevilla* have lighter green-colored leaves than plants of 'Red Riding Hood'.
4. Plants of the new *Mandevilla* have slightly smaller flowers than plants of 'Red Riding Hood'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the bottom of the sheet comprises a side perspective view of a typical flowering plant of 'FG1PK' grown in a container.

The photograph at the top of the sheet is a close-up view of typical flowers of a plant of 'FG1PK'.

DETAILED BOTANICAL DESCRIPTION

Plants used for the aforementioned photographs and following description were grown during the spring and early summer in one-gallon containers in a polyethylene-covered greenhouse in Hawthorne, Fla. and under conditions which closely approximate commercial production conditions. During the production of the plants, day temperatures averaged 29° C. and night temperatures averaged 21° C. Plants were eight months old when the photographs and description were taken. Plants were pinched one time. In the following description, color references are made to The Royal Horticultural Society Colour Chart, 2007 Edition, except where general terms of ordinary dictionary significance are used.

Botanical classification: *Mandevilla splendens* 'FG1PK'.

Parentage: Naturally-occurring branch mutation of *Mandevilla splendens* 'DIP 79', disclosed in U.S. Plant Pat. No. 19,698.

Propagation:

*Type.*—By tip cuttings.

*Time to initiate roots, summer.*—About 18 days at 29° C.

*Time to initiate roots, winter.*—About three weeks at 24° C.

*Time to produce a rooted young plant, summer.*—About 40 days at 29° C.

*Time to produce a rooted young plant, winter.*—About 50 days at 24° C.

*Root description.*—Fibrous, medium in thickness; white in color.

*Rooting habit.*—Moderate branching; medium density.

Plant description:

*Plant and growth habit.*—Upright, moderately vining and relatively compact plant habit; vigorous growth habit; freely branching habit with about five primary lateral branches, primary lateral branches with two to three secondary branches; dense and bushy appearance; pinching enhances lateral branch development.

*Plant height.*—About 21 cm.

*Plant diameter (spread).*—About 40 cm by 48 cm.

*Lateral branch description.*—Length: About 32 cm. Diameter: About 5 mm. Internode length: About 2.1 cm. Strength: Flexible, strong. Texture, young stems: Sparsely pubescent. Texture, developed stems: Woody, glabrous. Color, young stems: Close to 146C. Color, developed stems: Close to 199A.

Foliage description:

*Arrangement.*—Opposite, simple.

*Length.*—About 7 cm.

*Width.*—About 4.2 cm.

*Shape.*—Elliptical.

*Apex.*—Acute to acuminate.

*Base.*—Obtuse.

*Margin.*—Entire.

*Texture, upper and lower surfaces.*—Smooth, glabrous; leathery.

*Venation pattern.*—Pinnate, arcuate.

*Color.*—Developing leaves, upper surface: Close to 137B. Developing leaves, lower surface: Close to 146B. Fully expanded leaves, upper surface: Close to 139A; venation, close to 139B. Fully expanded leaves, lower surface: Close to 146B; venation, close to 146C.

*Petioles.*—Length: About 1.7 cm. Diameter: About 2 mm. Texture, upper and lower surfaces: Smooth, glabrous. Color, upper surface: Close to 146C. Color, lower surface: Close to 146D.

Flower description:

*Flower type and habit.*—Single salverform flowers; flowers arranged in loose terminal and axillary racemes; flowers face outwardly and upright; freely flowering habit with about 35 to 40 flowers developing per plant.

*Natural flowering season.*—Plants of the new *Mandevilla* begin flowering about three months after planting and flower continuously year-round in Florida.

*Flower longevity on the plant.*—Flowers last about four to five days; flowers not persistent.

*Fragrance.*—None detected.

*Inflorescence height.*—About 9 cm.

*Inflorescence diameter.*—About 5 cm.

*Flowers.*—Appearance: Flared trumpet, corolla fused, five-parted; petals imbricate; flowers salverform and roughly star-shaped. Diameter: About 7.3 cm. Depth (length): About 6.6 cm. Throat diameter: About 1.6 cm. Tube length: About 5.4 cm. Tube diameter, mid-section: About 1.4 cm. Tube diameter, base: About 5 mm.

*Flower buds.*—Length: About 7.2 cm. Diameter: About 1.4 cm. Shape: Cylindrical, pointed. Color: Close to 62B, 62C and 62D; darkest towards the apex.

*Corolla.*—Arrangement: Single whorl of five petals, fused into flared trumpet; petals imbricate. Petal lobe length: About 3.4 cm. Petal lobe width: About 2.8 cm. Petal lobe shape: Roughly elliptical. Petal apex: Acuminate; apices reflexed. Petal margin: Entire, slightly sinuate. Petal texture, upper and lower surfaces: Smooth, glabrous; velvety. Throat and tube texture: Smooth, glabrous. Color: Petal, when opening, upper surface: Close to 68A to 68B. Petal, when opening, lower surface: Close to 63C to 63D. Petal, fully opened, upper surface: Close to 63B, 63C and 63D, marbled; venation, close to 63B. Petal, fully opened, lower surface: Close to 63D and 65C to 65D, marbled; venation, close to 63D. Throat: Close to 170B; thin stripes, close to 13B; venation, close to 170B. Tube: Close to 63D and 65C to 65D, streaked; towards the base, close to 145D; venation, close to 65D.

*Sepals.*—Arrangement and appearance: Five per flower in a single whorl; fused towards the base. Length: About 7 mm. Width: About 2 mm. Shape: Lanceolate. Apex: Acute. Margin: Entire. Texture, upper and lower surfaces: Smooth, glabrous. Color, upper surface: Close to 145C. Color, lower surface: Close to 145B.

*Peduncles.*—Length: About 2.9 cm. Diameter: About 1.5 mm. Texture: Smooth, glabrous. Strength: Flexible, but strong. Angle: About 30 to 45° from the stem axis. Color: Close to 146C.

*Pedicels.*—Length: About 1.2 cm to 2 cm. Diameter: About 1.5 mm. Texture: Smooth, glabrous. Strength: Flexible, but strong. Angle: About 15 to 25° from the stem axis. Color: Close to 146C.

*Reproductive organs.*—Stamens: Quantity and arrangement: Typically five; filaments fused to corolla; anthers, connivent. Filament length: About 2 mm. Filament color: Close to 155C. Anther shape: Lanceolate. Anther length: About 9 mm. Anther color: Close to 161C. Pollen amount: Scarce to none. Pollen color: Close to 161D. Pistils: Quantity: Typically one. Pistil length: About 2.3 cm. Stigma shape: Rounded. Stigma color: Close to 146B. Style length: About 2 cm. Style color: Close to 145D. Ovary color: Close to 146D.

*Seeds and fruits.*—Seed and fruit production have not been observed on plants of the new *Mandevilla*.

Disease/pest resistance: Plants of the new *Mandevilla* have been noted to be somewhat resistant to Fusarium. Plants of the new *Mandevilla* have not been noted to resistant to pests and other pathogens common to *Mandevilla* plants.

Temperature tolerance: Plants of the new *Mandevilla* have been observed to tolerate temperatures from about 1° C. to about 43° C.

It is claimed:

1. A new and distinct *Mandevilla* plant named 'FG1PK' as illustrated and described.

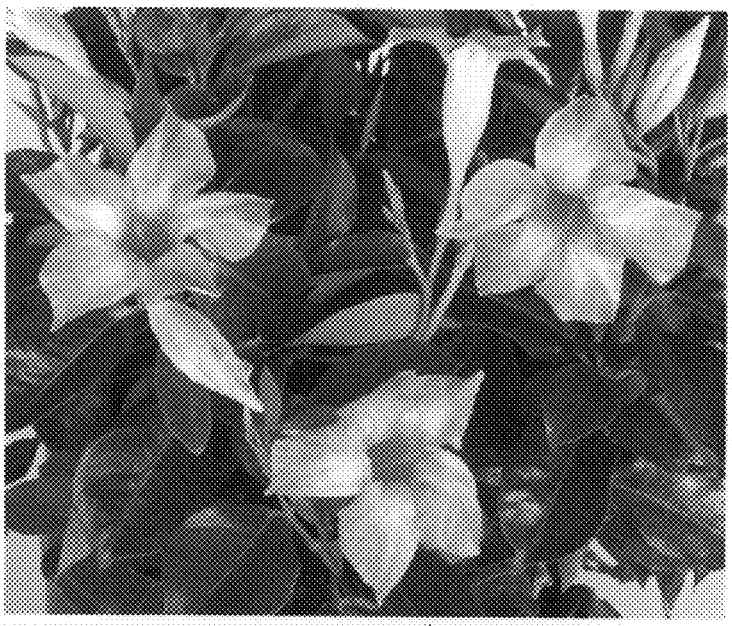
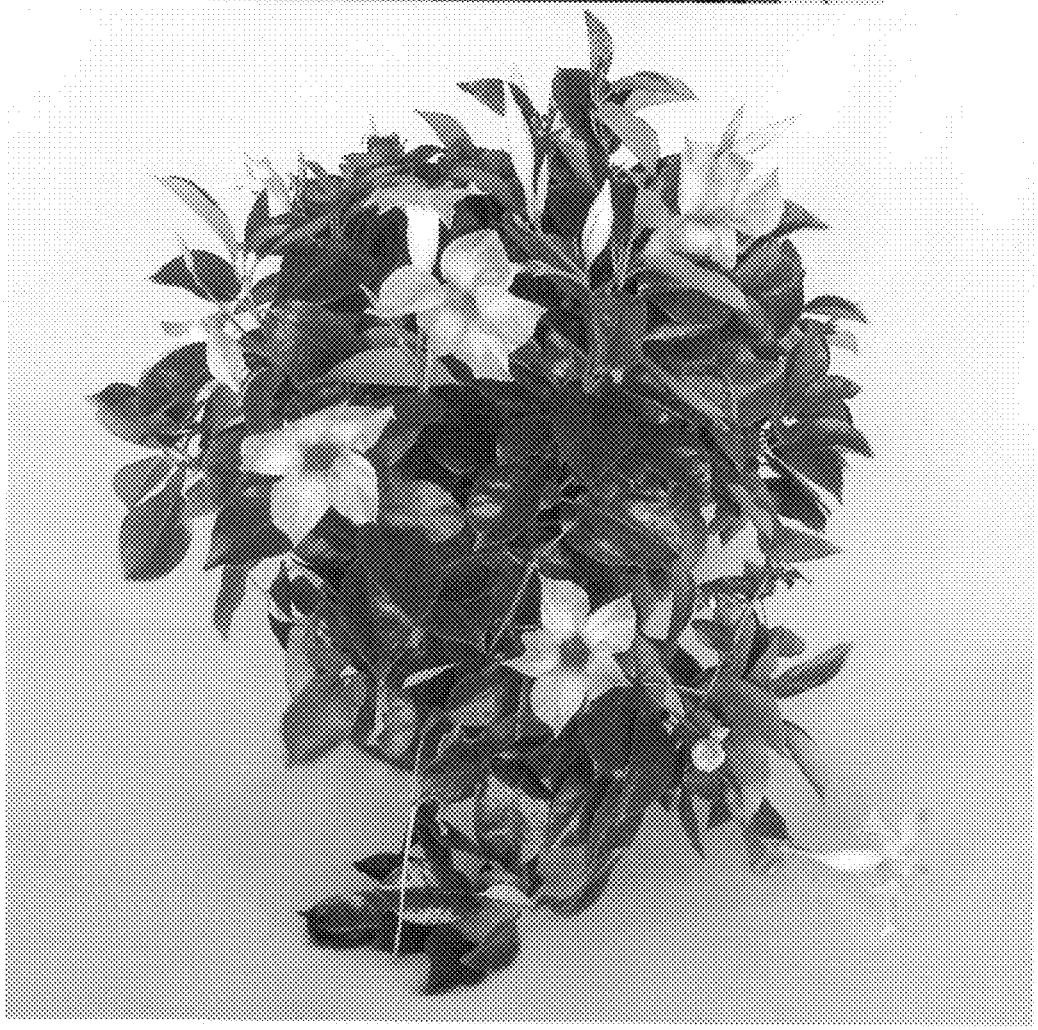

* * * * *